United States Patent

Tan et al.

[11] Patent Number: 6,077,527
[45] Date of Patent: Jun. 20, 2000

[54] ENHANCER TOLERANT PRESSURE SENSITIVE ADHESIVES FOR TRANSDERMAL DRUG DELIVERY

[75] Inventors: Hock S. Tan, Old Bridge; Ingrid Zhang, Somerville; Susan Lydzinski, Belle Mead; Peter L. Merkel, Long Valley; Paul Foreman, Somerville; Smita Shah, Edison; Rama S. Chandran, Bridgewater, all of N.J.

[73] Assignee: National Starch and Chemical Investment Holding Corporation, Wilmington, Del.

[21] Appl. No.: 08/958,862

[22] Filed: Oct. 28, 1997

[51] Int. Cl.[7] ........................................................ A61F 13/02
[52] U.S. Cl. ........................ 424/448; 526/304; 526/306; 526/303.1; 428/343; 428/355; 428/515; 428/520; 604/304; 604/308
[58] Field of Search ..................... 526/304, 306, 526/303.1; 428/343, 355, 515, 520; 604/304, 308; 424/448

[56] References Cited

U.S. PATENT DOCUMENTS

| | | | |
|---|---|---|---|
| 3,558,574 | 1/1971 | Doehnert | 260/78.5 |
| 4,822,676 | 4/1989 | Mudge | 428/343 |
| 5,223,261 | 6/1993 | Nelson et al. | 424/443 |
| 5,573,778 | 11/1996 | Therriault et al. | 424/448 |

FOREIGN PATENT DOCUMENTS

| | | |
|---|---|---|
| 0 600 428 A1 | 6/1994 | European Pat. Off. . |
| 0 455 458 B1 | 1/1996 | European Pat. Off. . |
| 9-310050 | 12/1997 | Japan . |

*Primary Examiner*—Michael A. Williamson
*Attorney, Agent, or Firm*—Lydia T. McNally

[57] ABSTRACT

Pressure sensitive adhesive compositions for use in transdermal drug delivery systems comprising an adhesive composition which is tolerant to plasticization by cutaneous penetration enhancers contained in the transdermal drug formulation are disclosed. Specifically, the pressure sensitive adhesive composition of the present invention comprises an acrylic copolymer prepared from (i) at least 40% by weight of th total monomer composition of alkyl acrylate monomers with a Tg of $-90$ to $0°$ C., (ii) 0–15% by weight of the total monomer composition of monomers with a Tg of 0 to $250°$ C., and (iii) 10–60% by weight of the total monomer composition of substituted acrylamides or methacrylamides having the structural formula:

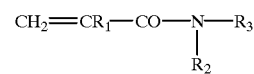

wherein
  $R_1$ is H or $CH_3$,
  $R_2$ is H or $CH_3$, and
  $R_3$ is (a) $CH_3$,
    (b) $C(CH_3)_2$—$(CH_2)_n$—$CH_3$ where n is 0 through 17, or
    (c) substituents of the formula:

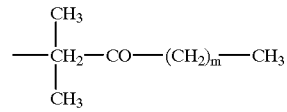

where m is 0 through 10,
and optionally
  (iv) at least 0.2% by weight of acrylic monomers containing at least one group having a reactive hydrogen, and (v) 0.01–2% by weight of a chelated metal alkoxide crosslinker to (i), (ii) and (iii).

17 Claims, No Drawings

ENHANCER TOLERANT PRESSURE SENSITIVE ADHESIVES FOR TRANSDERMAL DRUG DELIVERY

FIELD OF INVENTION

This invention relates to pressure sensitive adhesive compositions for use in transdermal drug delivery systems wherein the adhesive composition is tolerant to plasticization by cutaneous penetration enhancers contained in the transdermal drug formulation.

BACKGROUND OF THE INVENTION

A typical transdermal drug delivery patch comprises a flexible backing on which are applied, either as one layer or in spatial separation: a pressure sensitive adhesive, the desired pharmaceutically active drug, and cutaneous penetration enhancers. The cutaneous penetration enhancers are chemicals that enhance the permeation of the drug compounds into the skin to achieve the desired delivery rate. Chemical enhancers useful in transdermal drug delivery applications are well documented and fall into the categories of alcohols, fatty acid esters, fatty acids, amides, sulfoxides, polyols and surfactants. Such enhancers preferably have molecular weights in the range of 20 to 20,000.

Acrylic adhesives are well suited for transdermal drug delivery applications because they can be synthesized with inherent pressure-sensitive properties, and are conformable and adherable to human skin under a range of conditions for an extended period of time. However, when they are compounded with enhancers commonly used in transdermal patches, they may lose their pressure sensitive adhesive properties, such as tack, peel adhesion, and shear adhesion, due to either plasticization of the adhesive by the enhancers or migration of the enhancers through the adhesive to the patch surface. The plasticization by enhancers results in loss of cohesive strength and is evidenced by a large decrease in shear adhesion. The migration of enhancers to the adhesive-skin bond interface causes the transdermal patches to lose tack and peel adhesion. Although controlled migration/release of enhancers is desired to help drug permeation into the skin, a fast, uncontrolled migration of enhancers to the bond interface results in phase separation between the enhancer and the adhesive and is not desired.

"Migration of enhancers" as used in the present application refers to the fast, uncontrolled migration to the bond interface, which is disadvantageous and undesirable in drug delivery applications. "Resistant to migration of enhancers" means the adhesive has the ability to resist the undesired migration of enhancers. "Tolerant" means resistant to plasticization by chemical enhancers such that the adhesive, when compounded with the chemical enhancers, maintains its adhesive properties.

Therefore, the desired acrylic adhesive for transdermal drug delivery applications should be tolerant to plasticization by chemical enhancers so that adhesive integrity can be maintained, and resistant to migration of enhancers so that the pressure sensitive tackiness and adhesion can be maintained.

Several approaches have been taken in attempts to make adhesives more enhancer tolerant. One such method, disclosed in U.S. Pat. No. 5,573,778, has been to graft polystyrene onto an acrylic adhesive. This approach, however, has a number of disadvantages, which include incompatibility with many types of enhancers and drugs and the loss of adhesive properties over time when the enhancers are depleted from the system due to diffusion into the skin.

Another approach, described in European Patent Application 455458, has been to post-cure the adhesive with an electron beam which reportedly causes the adhesive to be tolerant of alcohol-based enhancers used in transdermal drug delivery devices. However, this reference does not disclose if this method works for other classes of enhancers, i.e. fatty acid esters, glycol esters, or amides.

U.S. Pat. Nos. 4,822,676 and 3,558,574 disclose the inclusion of t-octyl acrylamide and diacetone acrylamide, respectively, in pressure sensitive adhesive acrylic copolymer compositions. These references do not disclose the use of these compositions with cutaneous penetration enhancers.

Attempts have also been made to reduce the loss of adhesive integrity by increasing the level of crosslinking in the adhesive. Although crosslinking does increase the cohesive strength, the adhesive often loses its tack and peel adhesion, and thus does not adhere well to the skin.

Accordingly, it is the objective of the present invention to provide a pressure sensitive adhesive which possesses the ability to tolerate enhancer plasticization and to resist uncontrolled enhancer migration.

SUMMARY OF THE INVENTION

The object of the present invention is to provide a pressure sensitive adhesive composition which, when compounded with typical cutaneous penetration enhancers in transdermal applications, provides and maintains appropriate pressure sensitive properties over time.

Another object of the present invention is to provide a pressure sensitive adhesive composition into which may be incorporated functional amounts of cutaneous penetration enhancers without the disadvantages of plasticizing the adhesive and/or migration of the enhancers.

It has been found in accordance with the present invention, that adhesives having these desired properties can be obtained via polymerization of substituted acrylamides or methacrylamides, along with other commonly used acrylates such as 2-ethylhexyl acrylate, butyl acrylate, acrylic acid, and vinyl monomers such as vinyl acetate.

This invention is directed to a pressure sensitive adhesive composition comprising an acrylic copolymer prepared from (i) at least 40% by weight of the total monomer composition of alkyl acrylate monomers with a Tg of −90 to 0° C., (ii) 0–15% by weight of the total monomer composition of monomers with a Tg of 0 to 250° C., and (iii) 10–60% by weight of the total monomer composition of substituted acrylamides or methacrylamides having the structural formula:

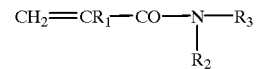

where
- $R_1$ is H or $CH_3$,
- $R_2$ is H or $CH_3$, and
- $R_3$ is (a) $CH_3$,
  - (b) $C(CH_3)_2$—$(CH_2)_n$—$CH_3$ where n is 0 through 17, or
  - (c) substituents of the formula:

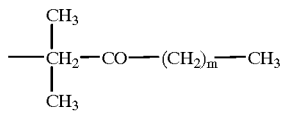

where m is 0 through 10.

This copolymer, when compounded with typical cutaneous penetration enhancers in transdermal applications, provides and maintains appropriate pressure sensitive properties over time, without the disadvantages of plasticizing the adhesive and/or migration of enhancers.

Optionally, pressure sensitive adhesive compositions of the present invention may include (iv) at least 0.2% by weight of the total monomer composition of acrylic monomers containing at least one group having a reactive hydrogen, and (v) 0.01–2% by weight of the total monomer composition of a chelated metal alkoxide crosslinker to (i), (ii) and (iii).

DETAILED DESCRIPTION OF THE INVENTION

This invention is directed to a pressure sensitive adhesive composition comprising an acrylic copolymer prepared from (i) at least 40% by weight of the total monomer composition of alkyl acrylate monomers with a Tg of –90 to 0° C., (ii) 0–15% by weight of the total monomer composition of monomers with a Tg of 0 to 250° C., and (iii) 10–60% by weight of the total monomer composition of substituted acrylamides or methacrylamides having the structural formula:

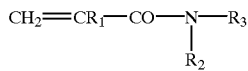

where
- $R_1$ is H or $CH_3$,
- $R_2$ is H or $CH_3$, and
- $R_3$ is (a) $CH_3$,
  - (b) $C(CH_3)_2$—$(CH2)_n$—$CH_3$ where n is 0 through 17, or
  - (c) substituents of the formula:

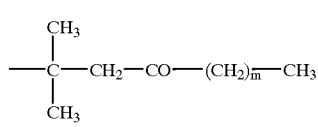

where m is 0 through 10.

The acrylic monomers which comprise component (i) have a Tg of –90 to 0° C., and are acrylic acid esters of alcohols having up to about 18 carbon atoms. The preferred alkyl acrylates have about 4 to 10 carbon atoms in the alkyl groups, and include butyl, amyl, hexyl, 2-ethylhexyl, octyl, dedcyl, and dodecyl acrylates, and isomers thereof.

The acrylic monomers of component (i) are present in an amount of at least 40% by weight based upon the total monomer weight of the composition and preferably 40–80% by weight.

The monomers which comprise component (ii) have a Tg of 0 to 250° C. and preferably include vinyl acetate, methyl acrylate, and methyl methacrylate.

The monomers which comprise component (ii) are present in an amount of 0–15% by weight based upon the total monomer weight of the composition, preferably 5–10% by weight.

Examples of the substituted acrylamides or methacrylamides (iii) described in the present invention includes N-tertiary octyl acrylamide (t-octyl acrylamide), dimethyl acrylamide, diacetone acrylamide, N-tertiary butyl acrylamide (t-butyl acrylamide), and N-isopropyl acrylamide (i-propyl acrylamide).

The substituted acrylamides or methacrylamides which comprise component (iii) are present in an amount of 10–60% by weight based upon the total monomer weight of the composition, preferably 15–50% by weight.

The pressure sensitive adhesive compositions of the present invention optionally may include (iv) acrylic monomers containing a group having a reactive hydrogen and (v) a chelated metal alkoxide crosslinker to (i), (ii), and (iii).

Examples of acrylic monomers of component (iv), containing at least one group having a reactive hydrogen, include acrylic acid, methacrylic acid, and hydroxylethyl acrylate. These acrylic monomers of component (iv) are present in an amount of at least 0.2% by weight based upon the total weight of the monomer composition, preferably 0.2–10%.

The preferred chelated metal alkoxides crosslinker of component (v) are chelated aluminum esters such as aluminum acetylacetonate, and chelated titanium alkoxides such as titanium acetylacetonate.

The chelated metal alkoxides of component (v) are present in an amount of 0.01–2% by weight based upon the total monomer composition, preferably 0.05–1%.

To demonstrate the advantageous properties of the adhesive compositions of the present invention, various pressure sensitive adhesive compositions were prepared having the compositions described in the following Examples.

These examples are merely provided to help illustrate the subject invention, and are not intended to, and should not in any way be construed to, limit the subject invention as defined in the claims of this application.

EXAMPLE 1

An initial charge containing 2.1 g t-octyl acrylamide, 16.76 g butyl acrylate, 5.0 g vinyl acetate, 1.0 g acrylic acid, 39.9 g ethyl acetate (solvent) and 0.04 g benzoyl peroxide (polymerization initiator) was prepared and charged to a 1-liter four-neck round bottom flask equipped with stainless steel stirrer, thermometer, condenser, water bath, slow addition funnels. The initial charge was heated to reflux, and held at reflux for 10 minutes. A monomer mix containing 63.24 g butyl acrylate, 4.0 g acrylic acid, 7.9 g t-octyl acrylamide and an initiator mix containing 15.8 g ethyl acetate, 11.3 g heptane, 1.3 g toluene, 0.46 g isopropanol, and 0.63 g benzoyl peroxide were prepared. The monomer mix and the initiator mix were simultaneously and uniformly slow added to the initial charge over 2 and 4 hours respectively while maintaining reflux. At the end of the monomer/initiator slow add, the contents were held at reflux for 2 hours after which the contents were cooled to room temperature while adding a dilution solvent containing 4.5 g ethyl acetate, 27.7 g heptane, 1.8 g toluene and 23.0 g isopropanol. The solution polymer was discharged. A small amount of aluminum acetyl acetonate, ranging from 0.15 to 0.46 parts per total monomers charged, was added after the reaction completed, to obtain optimum performance of pressure sensitive properties.

EXAMPLES 2–8

Using the general procedure described above, six additional adhesives were prepared varying the amounts and/or compositions of the monomers. The major monomers and their respective amounts (in parts per hundred of total monomers weight) are shown in Table I (Examples 2 to 7).

As a comparison, one additional adhesive was prepared without any substituted acrylamides. This serves as a control and is shown in Table I as Example 8.

TABLE I

Polymer Examples

| Example | 1 | 2 | 3 | 4 | 5 | 6 | 7 | 8 |
|---|---|---|---|---|---|---|---|---|
| Remarks | | | | | | | | Control |
| t-octyl acrylamide | 10 | 30 | 40 | | | | | |
| dimethyl acrylamide | | | | 30 | | | | |
| diacetone acrylamide | | | | | 30 | | | |
| t-butyl acrylamide | | | | | | 30 | | |
| i-propyl acrylamide | | | | | | | 30 | |
| i-butyl methacrylate | | | | | | | | 30 |
| 2-ethylhexyl-acrylate | | 30 | 53 | 30 | 30 | | | 30 |
| butyl acrylate | 80 | 33 | | 33 | 33 | 33 | 33 | 33 |
| vinyl acetate | 5 | 5 | 5 | 5 | 5 | 5 | 5 | 5 |
| acrylic acid | 5 | 2 | 2 | 2 | 2 | 2 | 2 | 2 |
| Calculated $T_g$, °C. | −37 | −31 | −28 | −27 | −31 | −34 | −28 | −31 |

Each of adhesives prepared according to Examples 1–8 were compounded with one of four different chemical enhancers, coated on a 2-mil thick polyester film to give a 1-mil thick dry adhesive, and then tested for pressure sensitive adhesive properties. The four systems of chemical enhancers tested were: i) 5% glycerol monolaurate dissolved in an equivalent amount of a $C_{12}$ linear alcohol, ii) 10% of isopropyl myristate, iii) 10% of oleic acid, and iv) 15% of N,N-diethyl m-toluamide (% given were weight percentage added to the polymer adhesive, based on dry adhesive).

Four standard pressure sensitive adhesive tests were performed: peel adhesion on stainless steel panel (measured in oz/in) at tape-on-panel dwell time of 20 min and 24 h in accordance with Pressure Sensitive Tape Council's Test Method PSTC-1; 8-psi shear cohesion (or holding power, measured in h) in accordance with PSTC-7 (contact area=1 in×0.5 in, mass=2000 g); and probe tack (measured in g) measured using Texture Analyzer (manufactured by Stable Micro Systems, Surrey, England) with a 7 mm diameter stainless steel flat end probe, and contact time of 1 s. The peak of force profile generated by the Texture Analyzer's accompanied computer software, Texture Expert, was taken as the probe tack. The results are tabulated in Tables II, III, IV, and V.

Desirable enhancer-tolerant properties are defined by the values that fall into the following ranges:

| | | |
|---|---|---|
| i) | 20 min peel = | 18 to 45 oz/in |
| ii) | 24 h peel = | 25 to 65 oz/in |
| iii) | 8 psi shear = | 1.5 to 50.0 h |
| iv) | Probe tack = | 200 to 700 g |

Table II shows that adhesive compositions of the present invention, prepared with substituted acrylamides of t-octyl acrylamide (Examples 1, 2 and 3), dimethyl acrylamide (Example 4), diacetone acrylamide (Example 5), t-butyl acrylamide (Example 6), and isopropyl acrylamide (Example 7), all have desirable enhancer-tolerant properties when compounded with 5% glycerol monolaurate/5% lauryl alcohol. The control (Example 8 in Table II), whose composition is without any substituted acrylamides, does not have the desirable enhancer-tolerant properties. For example, with respect to 24 hour peel, Examples 1–7 have values ranging from 27–61 oz/in, which falls into the desired range of 25–65 oz/in. The control, Example 8, shows a value of 0.3, which is far outside the desired range. Clearly the adhesives of the present invention, which comprise substituted acrylamides, provide desirable enhancer-tolerant properties when compared to adhesives prepared without substituted acrylamides.

TABLE II

Effects of 5% Glycerol Monolaurate in 5% $C_{12}$ linear alcohol

Polymer Example

| | 1 | 2 | 3 | 4 | 5 | 6 | 7 | 8 |
|---|---|---|---|---|---|---|---|---|
| Crosslinker, % | 0.46 | 0.46 | 0.46 | 0.15 | 0.15 | 0.23 | 0.23 | 0.46 |
| 20 min Peel | 19 | 39 | 31 | 41 | 30 | 42 | 37 | 0.1 |
| 24 h Peel | 27 | 42 | 43 | 60 | 43 | 60 | 61 | 0.3 |
| 8 psi Shear | 5.9 | 6.1 | 8.2 | 4.2 | 5.3 | 2.0 | 35.0 | 0.0 |
| Probe Tack | 234 | 274 | 314 | 273 | 295 | 336 | 233 | 4 |

Tables III, IV and V show the results of the pressure sensitive adhesive tests using select adhesive compositions of the present invention compounded with the chemical enhancers 10% isopropyl myristate, 10% oleic acid and 15% N,N-diethyl m-toluamide.

Table III shows that adhesive compositions of the present invention, comprising substituted acrylamides, have desirable enhancer-tolerant properties when compounded with the chemical enhancer isopropyl myristate. The acrylamides tested were t-octyl acrylamide (Examples 1 and 2), dimethyl acrylamide (Example 4), and diacetone acrylamide (Example 5) all of which produced better results than the control (Example 8), whose composition is without any substituted acrylamides. Although the control did show desirable probe tack, it did not have the desirable enhancer-tolerant properties of peel adhesion and shear cohesion.

TABLE III

Effects of 10% Isopropyl Myristate

| | Polymer Example | | | | |
|---|---|---|---|---|---|
| | 1 | 2 | 4 | 5 | 8 |
| Crosslinker % | 0.23 | 0.23 | 0.15 | 0.15 | 0.23 |
| 20 min Peel | 20 | 27 | 31 | 30 | 5 |
| 24 h Peel | 39 | 41 | 44 | 41 | 14 |
| 8 psi Shear | 5.5 | 17.3 | 14.5 | 18.8 | 1.2 |
| Probe Tack, g | 295 | 294 | 229 | 376 | 300 |

Table IV shows that adhesive compositions, in accordance with the present invention, have desirable enhancer-tolerant properties when compounded with the chemical enhancer oleic acid. Adhesive compositions prepared with substituted acrylamides of t-octyl acrylamide (Examples 1, 2 and 3), dimethyl acrylamide (Example 4), and diacetone acrylamide (Example 5) all have desirable enhancer-tolerant properties when compounded with oleic acid. The control (Example 8 in Table IV), whose composition is without any substituted acrylamides, had reasonable probe tack property, but did not have the desirable enhancer-tolerant properties of peel adhesion and shear cohesion.

TABLE IV

Effects of 10% Oleic Acid

| | Polymer | | | | | |
|---|---|---|---|---|---|---|
| | 1 | 2 | 3 | 4 | 5 | 8 |
| Crosslinker % | 0.46 | 0.46 | 0.46 | 0.46 | 0.46 | 0.46 |
| 20 min Peel | 20 | 28 | 32 | 36 | 31 | 3 |
| 24 h Peel | 27 | 41 | 40 | 52 | 41 | 6 |
| 8 psi Shear | 1.6 | 5.5 | 11.4 | 7.8 | 7.9 | 0.4 |
| Probe Tack, g | 262 | 422 | 364 | 315 | 448 | 274 |

Results in Table V show that an adhesive composition in accordance with the present invention, comprising t-octyl acrylamide (Example 2) has desirable enhancer-tolerant properties when compounded with chemical enhancer of N,N-diethyl m-toluamide. The control (Example 8), whose composition contains no substituted acrylamides, had reasonable probe tack property, but did not have the desirable enhancer-tolerant properties of peel adhesion and shear cohesion.

TABLE V

Effects of 15% N,N-Diethyl m-Toluamide

| | Polymer | |
|---|---|---|
| | 2 | 8 |
| Crosslinker % | 0.46 | 0.46 |
| 20 min Peel | 30 | 15 |
| 24 h Peel | 39 | 20 |
| 8 psi Shear | 10.2 | 2.1 |
| Probe Tack, g | 410 | 322 |

The results shown in tables 2–5 indicate that adhesives comprising substituted acrylamides in accordance with the present invention have desirable enhancer tolerant properties when compared to a control which does not comprise substituted acrylamides.

We claim:

1. A pressure sensitive adhesive composition comprising an acrylic copolymer prepared from components consisting essentially of (i) at least 40% by weight of the total monomer composition of alkyl acrylate monomers with a Tg of −90 to 0° C., (ii) 0–15% by weight of the total monomer composition of monomers with a Tg of 0 to 250° C., and (iii) 10–60% by weight of the total monomer composition of substituted acrylamides or methacrylamides having the structural formula:

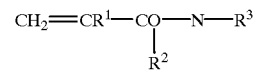

where $R^1$ is H or $CH_3$, $R^2$ is H or $CH_3$, and $R^3$ is (a) $CH_3$, (b) $C(CH_3)_2$—$(CH_2)_n$—$CH_3$ where n is 0 through 17, or (c) substituents of the formula:

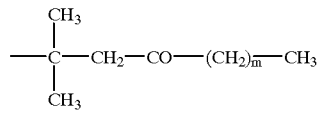

where m is 0 through 10, (i) 0.01–2% by weight of the total monomer composition of a chelated metal alkoxide crosslinker, to (i), (ii) and (iii), wherein the chelated metal is aluminum or titanium, and, (v) optionally, at least 0.2% by weight of the total monomer composition of acrylic monomers containing at least one group having a reactive hydrogen.

2. A pressure sensitive adhesive composition according to claim 1 wherein the acrylic monomers having a Tg of −90 to 0° C. are acrylic acid esters of alcohols having up to about 18 carbon atoms.

3. A pressure sensitive adhesive composition according to claim 2 wherein the acrylic monomers have 4 to 10 carbon atoms in the alkyl groups.

4. A pressure sensitive adhesive composition according to claim 2 wherein the acrylic monomers are selected from the group consisting of butyl, amyl, hexyl, 2-ethylhexyl, octyl acrylates, dedcyl acrylates, dodecyl acrylates, and isomers thereof.

5. A pressure sensitive adhesive composition according to claim 1 wherein the monomers having a Tg of 0 to 250° C. comprise monomers selected from the group consisting of vinyl acetate, methyl acrylate, and methyl methacrylate.

6. A pressure sensitive adhesive composition according to claim 1 wherein the substituted acrylamides are selected from the group consisting of N-tertiary octyl acrylamide, t-octyl acrylamide, dimethyl acrylamide, diacetone acrylamide, N-tertiary butyl acrylamide, t-butyl acrylamide, N-isopropyl acrylamide and i-propyl acrylamide.

7. A pressure sensitive adhesive composition according to claim 1 wherein the acrylic monomers containing at least one group having a reactive monomer are selected from the group consisting of acrylic acid, methacrylic acid, and hydroxylethyl acrylate.

8. A pressure sensitive adhesive composition according to claim 1 wherein the chelated metal alkoxides are chelated aluminum esters or chelated titanium alkoxides.

9. A pressure sensitive adhesive composition according to claim 1 wherein the chelated metal alkoxides are selected from the group consisiting of aluminum acetylacetonate and titanium acetylacetonate.

10. A transdermal drug delivery system comprising an adhesive according to claim 1.

11. A transdermal drug delivery system comprising a pharmaceutically active composition, cutaneous penetration enhancers and a pressure sensitive adhesive composition according to claim 1.

12. A transdermal drug delivery system according to claim 11 wherein said cutaneous penetration enhancers are selected from the group consisting of alcohols, fatty acid esters, fatty acids, amides, sulfoxides, polyols and surfactants.

13. A transdermal drug delivery system according to claim 12 wherein said cutaneous penetration enhancers have a molecular weight of 20 to 20,000.

14. A pressure sensitive adhesive composition comprising an acrylic copolymer prepared from components consisting essentially of
 (i) 40–80% by weight of the total monomer composition of alkyl acrylate monomers with a Tg of −90 to 0° C.,
 ii) 5–10% by weight of the total monomer composition of monomers with a Tg of 0 to 250° C., and
 (iii) 15–50% by weight of the total monomer composition of substituted acrylamides or methacrylamides having the structural formula:

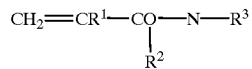

where
 $R^1$ is H or $CH_3$,
 $R^2$ is H or $CH_3$, and
 $R^3$ is (a) $CH_3$,
  (b) $C(CH_3)_2$—$(CH_2)_n$—$CH_3$ where n is 0 through 17, or
  (c) substituents of the formula:

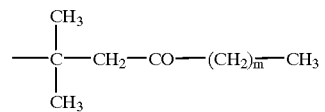

where m is 0 through 10,
 (iv) 0.01–2% by weight of the total monomer composition of a chelated metal alkoxide crosslinker, to (i), (ii) and (iii), wherein the chelated metal is aluminum or titanium, and, (v) optionally, at least 0.2% by weight of the total monomer composition of acrylic monomers containing at least one group having a reactive hydrogen.

15. A transdermal drug delivery system comprising an adhesive according to claim 14.

16. A transdermal drug delivery system comprising a pharmaceutically active composition, cutaneous penetration enhancers and a pressure sensitive adhesive composition according to claim 14.

17. A transdermal drug delivery system according to claim 16 wherein said cutaneous penetration enhancers are selected from the group consisting of alcohols, fatty acid esters, fatty acids, amides, sulfoxides, polyols and surfactants.

* * * * *